(12) United States Patent
Liu et al.

(10) Patent No.: US 10,813,647 B2
(45) Date of Patent: Oct. 27, 2020

(54) LEFT ATRIAL APPENDAGE OCCLUDER

(71) Applicant: LIFETECH SCIENTIFIC (SHENZHEN) CO., LTD, Shenzhen (CN)

(72) Inventors: Jie Liu, Shenzhen (CN); Shufei Xie, Shenzhen (CN); Li Yan, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 106 days.

(21) Appl. No.: 16/307,522

(22) PCT Filed: May 10, 2017

(86) PCT No.: PCT/CN2017/083725
§ 371 (c)(1),
(2) Date: Dec. 6, 2018

(87) PCT Pub. No.: WO2017/215371
PCT Pub. Date: Dec. 21, 2017

(65) Prior Publication Data
US 2019/0142431 A1   May 16, 2019

(30) Foreign Application Priority Data
Jun. 15, 2016 (CN) .......................... 2016 1 0423625

(51) Int. Cl.
*A61B 17/12* (2006.01)
*A61F 2/06* (2013.01)

(52) U.S. Cl.
CPC .... *A61B 17/12122* (2013.01); *A61B 17/1214* (2013.01); *A61B 17/12031* (2013.01);
(Continued)

(58) Field of Classification Search
CPC ........ A61B 17/12031; A61B 17/12172; A61B 17/12177; A61B 17/1214; A61F 2/06
See application file for complete search history.

(56) References Cited

U.S. PATENT DOCUMENTS

| 5,725,552 A | 3/1998 | Kotula et al. |
| 2011/0054515 A1* | 3/2011 | Bridgeman ........ A61B 17/0057 606/200 |

(Continued)

FOREIGN PATENT DOCUMENTS

| CN | 1384726 A | 12/2002 |
| CN | 202335893 U | 7/2012 |

(Continued)

OTHER PUBLICATIONS

International Search Report dated Aug. 9, 2017 in corresponding International Application No. PCT/CN2017/083725; 6 pages.
(Continued)

*Primary Examiner* — Jocelin C Tanner
(74) *Attorney, Agent, or Firm* — Maier & Maier, PLLC

(57) ABSTRACT

A left atrial appendage occluder which includes a closure disc, a mesh anchoring apparatus, and a thin-film body, connected to one another. The anchoring apparatus extends from the closure disc toward the distal end to form a conical part having a distal-end opening, and the conical part extends toward the proximal end and rolls up to form an anchoring part. The thin-film body is fixed on the outside surface of at least one part of the anchoring part, and part or all of it covers the distal-end opening. The left atrial appendage occluder is provided with the thin-film body on the anchoring apparatus, which constrains the deformation of different parts, and accordingly improves the radial supporting force of the occluder so as to prevent it from falling out after implantation.

20 Claims, 2 Drawing Sheets

(52) U.S. Cl.
CPC .. *A61B 17/12172* (2013.01); *A61B 17/12177* (2013.01); *A61F 2/06* (2013.01)

(56) References Cited

U.S. PATENT DOCUMENTS

| | | | |
|---|---|---|---|
| 2011/0160753 | A1 | 6/2011 | Bastin |
| 2012/0065667 | A1* | 3/2012 | Javois .............. A61B 17/12122 606/213 |
| 2013/0218193 | A1 | 8/2013 | Erzberger et al. |
| 2014/0142612 | A1* | 5/2014 | Li ................... A61B 17/12177 606/200 |

FOREIGN PATENT DOCUMENTS

| | | |
|---|---|---|
| CN | 102805654 A | 12/2012 |
| CN | 103598902 A | 2/2014 |
| CN | 104352260 A | 2/2015 |
| CN | 102908174 B | 3/2015 |
| CN | 104768476 A | 7/2015 |
| CN | 104856741 A | 8/2015 |
| CN | 104958087 A | 10/2015 |
| CN | 205758648 U | 12/2016 |

OTHER PUBLICATIONS

Chinese Notification to Grant Patent Right for Invention (Chinese NOA) dated Feb. 7, 2020, in connection with corresponding CN Application No. 201610423625.8 (3 pgs., including machine-generated English translation).
(Supplemental/Second) Chinese Search Report dated Jan. 14, 2020, in connection with corresponding CN Application No. 201610423625.8 (1 pg.).
(Original) Chinese Search Report dated Sep. 10, 2019, in connection with corresponding CN Application No. 201610423625.8 (2 pgs.).
(Second) Chinese Office Action dated Sep. 17, 2019, in connection with corresponding CN Application No. 201610423625.8 (24 pgs., including machine-generated English translation).
(First) Chinese Office Action dated Mar. 19, 2019, in connection with corresponding CN Application No. 201610423625.8 (17 pgs., including machine-generated English translation).

* cited by examiner

LEFT ATRIAL APPENDAGE OCCLUDER

FIELD

A medical device, and more particularly relates to a left atrial appendage occluder, which is delivered to a selected part of a human body by means of percutaneous puncture.

BACKGROUND

Percutaneous puncture has been used in treating diseases more and more. Various materials, devices and drugs may be placed in the heart and arteriovenous vessels of human by means of this technology. For example, an occluder may be put into a left atrial appendage to occlude an inlet of a cavity of the left atrial appendage and cut off all or most of blood flowing into the cavity of the left atrial appendage, so as to prevent a thrombus formed in the cavity of the left atrial appendage caused by atrial fibrillation and avoid apoplexy caused by the thrombus going up to a brain, or prevent systematic embolization resulted from the thrombus reaching other parts of the body through a human blood circulation system.

Left atrial appendage occluders include integrated occluders and split type occluders at the present. Each integrated occluder is required to be completely plugged into the cavity of the left atrial appendage. Each split type occluder includes a seal disc and an anchoring apparatus connected with the seal disc. The occluder is delivered to the inlet of the cavity of the left atrial appendage by means of a catheter and then spreads. The seal disc is used for covering the inlet to cut off all or most of blood flowing into the left atrial appendage. The anchoring apparatus is generally plugged into the inner wall of the cavity of the left atrial appendage or a tissue near the inlet, or is fixed in the cavity of the left atrial appendage by means of its extrusion force on the cavity wall of the left atrial appendage to locate an occluding disc at the above-mentioned inlet, so as to avoid falling out of the occluder and to avoid occlusion leakage as much as possible, thereby achieving a good occluding effect.

SUMMARY

For a split type left atrial appendage occluder, an anchoring apparatus may need to have a relatively high radial supporting force. Namely, when the occluder completely spreads in the cavity of a left atrial appendage, the anchoring apparatus may need to apply a relatively high extrusion force to the cavity wall of the left atrial appendage, otherwise, the anchoring apparatus may not be fixed in the cavity of the left atrial appendage, which causes displacement or undesired movement of the occluder.

When the anchoring apparatus is of a self-expandable mesh structure woven from weaving wires, and after the occluder is implanted into the left atrial appendage, the mesh wires can easily move due to the lack of mutual constraint, thus resulting in the deformation of the anchoring apparatus. In addition, as the mesh structure has a relatively low radial supporting force, the anchoring apparatus is fixed unstably, resulting in a potential danger of falling out of the device.

To solve the technical problems, which include, but are not limited to such a shortcoming as a relatively low radial supporting force of a mesh anchoring apparatus, exemplary embodiments described in the present application provides a left atrial appendage occluder.

A solution adopted to solve the technical problem is as follows: a left atrial appendage occluder is provided, including a seal disc and a mesh anchoring apparatus which are connected with each other. The anchoring apparatus extends from the seal disc towards the distal end to form a conical part having a distal-end opening, and the conical part rolls up towards the proximal end and then extends towards the proximal end to form an anchoring part. The left atrial appendage occluder further includes a thin-film body fixed on the outer surface of at least one part of the anchoring part, and part or all of it covers the distal-end opening.

In the left atrial appendage occluder, according to an exemplary embodiment of the present application, the thin-film body includes a spherical thin film which completely covers the distal-end opening and is fixed on the outer surface of at least one part of the distal end of the anchoring part.

In the left atrial appendage occluder, according to an exemplary embodiment of the present application, the thin-film body includes at least one annular thin film surrounding the opening, and each annular thin film is fixed on the outer surface of at least one part of the anchoring part and exposes the opening.

In the left atrial appendage occluder, according to an exemplary embodiment of the present application, the thin-film body is sutured or adhered onto the anchoring apparatus.

In the left atrial appendage occluder according to the embodiment of the present application, the thin-film body is made of polyester, PTFE (polytetrafluoroethylene), silicon resin, urethane, metal fibers or silica gel.

In the left atrial appendage occluder, according to an exemplary embodiment of the present application, the thin-film body has multiple open pores.

In the left atrial appendage occluder according to an exemplary embodiment of the present application, the aperture of each pore is about 65 to about 1000 microns.

In the left atrial appendage occluder, according to an exemplary embodiment of the present application, the aperture ratio of the thin-film body is at least about 20 percent.

In the left atrial appendage occluder, according to an exemplary embodiment of the present application, the anchoring part surrounds the conical part, and the suspended end of the anchoring part is inwards bent to form an approximately U-shaped convergent region.

In the left atrial appendage occluder, according to an exemplary embodiment of the present application, the anchoring part is provided with at least one barb, the suspended end of which faces to the seal disc.

In the left atrial appendage occluder, according to an exemplary embodiment of the present application, the suspended end of the at least one barb penetrates through the thin-film body.

In the left atrial appendage occluder, according to an exemplary embodiment of the present application, a distance from the edge of the proximal end of the thin-film body to the root part of each barb is about 1 mm to about 8 mm.

In the left atrial appendage occluder, according to an exemplary embodiment of the present application, when each barb penetrates through the thin-film body, the length beyond the thin-film body is about 1 mm to about 5 mm.

In the left atrial appendage occluder according to an exemplary embodiment of the present application, the thickness of a region, near each barb, of the thin-film body is greater than or equal to that of the rest region of the thin-film body.

In the left atrial appendage occluder according to an exemplary embodiment of the present application, the mesh structure is woven from multiple weaving wires, and at an intersection of two weaving wires of the mesh structure, the thin-film body is sutured onto the anchoring apparatus.

In the left atrial appendage occluder, according to an exemplary embodiment of the present application, a suture penetrates through the thin-film body, bypasses the intersection and is knotted to fix the thin-film body onto the anchoring device.

In the left atrial appendage occluder according to an exemplary embodiment of the present application, the thin-film body is fixed on the anchoring part on the mesh structure through multiple first suture points and multiple second suture points, the multiple first suture points surround the opening, and any one of the first suture points is closer to the opening than any one of the second suture points.

In the left atrial appendage occluder, according to an exemplary embodiment of the present application, the multiple first suture points and the multiple second suture points are respectively located on two circumferences coaxial with the anchoring apparatus.

In the left atrial appendage occluder according to the embodiment of the present application, the center axis of the seal disc and the center axis of the anchoring apparatus are located on the same straight line along a lengthwise direction.

In the left atrial appendage occluder according to the embodiment of the present application, another thin-film body is further arranged in an exemplary seal disc and has multiple open pores, and the aperture of each open pore is between about 65 and about 1000 microns.

After the left atrial appendage occluder of the present application is implanted into the left atrial appendage, the anchoring apparatus is implanted into the cavity of the left atrial appendage and cooperates with the left atrial appendage to fix the occluder. Compared with the way that the weaving wires are in direct contact with the cavity wall of the left atrial appendage, the way that the anchoring apparatus along with the thin-film body are in contact with the cavity wall of the left atrial appendage, and the first thin-film body enlarges the contact area by dozens of times, so that stress on the cavity wall of the left atrial appendage is more uniform, and stress of a unit area is lower, which avoids injury to the cavity wall of the left atrial appendage caused by extremely high partial stress. In exemplary embodiments of the present application, the anchoring apparatus of the present application is provided with the thin-film body, which can constrain the deformation of each part and accordingly improve the radial supporting force of the device so as to prevent the occluder from falling out after the implantation.

BRIEF DESCRIPTION OF THE DRAWINGS

The present application will be further described below in combination with accompanying drawings and embodiments. In the drawings.

DETAILED DESCRIPTION

A left atrial appendage occluder provided by the present application is of a split type structure, which includes a seal disc, a mesh anchoring part which is connected with the distal end of the seal disc and is in contact with the inner wall of a cavity of a left atrial appendage in a used state, and a first thin-film body, at least part of which is fixed on the outer surface of the distal end of the anchoring part. To understand technical features, objectives and effects of the present application more clearly, specific implementation modes of the present application are described now in detail as exemplary embodiments in combination with the exemplary drawings.

To describe the structure of the left atrial appendage occluder (hereinafter referred to as the occluder) more clearly, terms "distal end" and "proximal end" are defined here. The above-mentioned terms are commonly used terms in the field of interventional medical devices. Specifically, the "distal end" represents the end far away from an operator in a surgical process, and the "proximal end" represents the end close to the operator in the surgical process.

Figure 1:
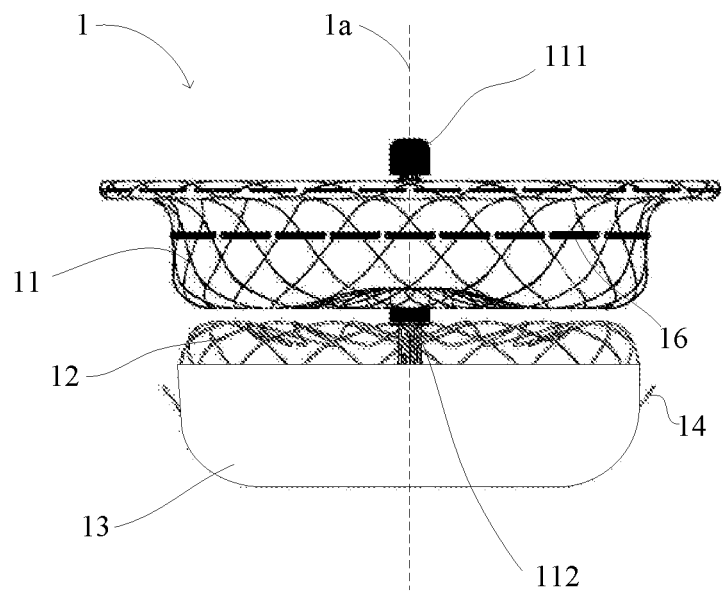
FIG. 1 is an exemplary structure schematic diagram of a left atrial appendage occluder according to a first embodiment of the present application.

Referring to exemplary FIG. 1, a left atrial appendage occluder 1 according to a first embodiment of the present application includes a seal disc 11, an anchoring apparatus 12 which is connected with each other, and a first thin-film body 13 arranged on the outer surface of the distal end of the anchoring apparatus 12. The first thin-film body 13 may be fixed on the anchoring apparatus 12. It should be noted that if no special instructions are provided in FIG. 1 and all the subsequent drawings, the occluders as shown in all the drawings are in a naturally expanded state by default.

The seal disc 11 may be woven from nickel-titanium metal wires or biocompatible macromolecular wires, and is located at the proximal end relative to the anchoring apparatus 12. The seal disc 11 has a proximal end portion 111 and a distal end portion 112. The above-mentioned metal wires or macromolecular wires are all accommodated in the two end portions. The structure and a manufacturing method of the seal disc 11 are based on the prior art, so that no more details will be described herein. For example, the structure and the manufacturing method may refer to an occluder structure and a relevant manufacturing method which are disclosed in U.S. Pat. No. 5,725,552A or CN102908174B. For example, the occluder may be a Patent Ductus Arteriosus (PDA) occluder.

Figure 2:
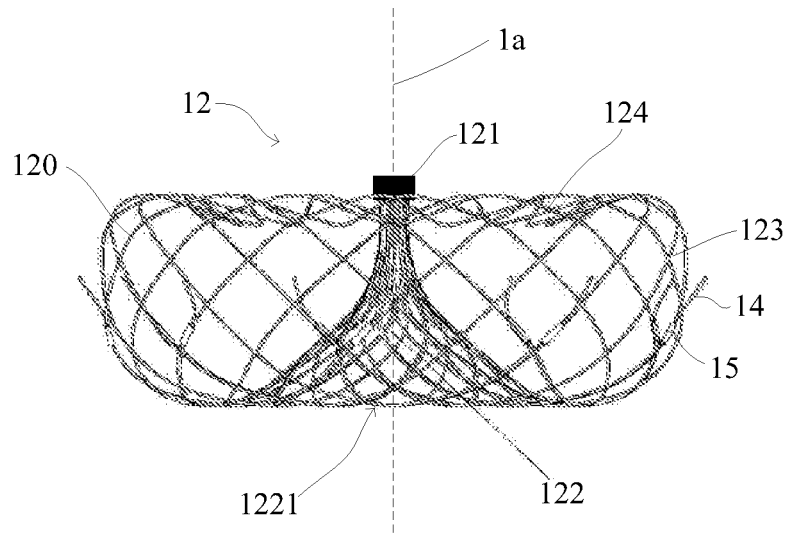
FIG. 2 is an exemplary structure schematic diagram of an anchoring apparatus in FIG. 1.

Referring to exemplary FIG. 1 and exemplary FIG. 2, the anchoring apparatus 12 may be of a woven mesh structure woven from nickel-titanium metal weaving wires or biocompatible macromolecular weaving wires 120. For example, the weaving wires 120 may be intersected in a one-press-one manner to form grids. One end of the anchoring apparatus 12 is converged to form a convergent end portion 121 which is connected with the distal end portion 112 of the seal disc 11, and the other end of the anchoring apparatus 12 extends towards the distal end at first to form a conical part 122 having a distal-end opening 1221 at the distal end, then rolls up towards the proximal end to form a U-shaped bend and extends towards the proximal end to form an anchoring part 123. The center axis of the anchoring apparatus 12 and the center axis of the seal disc 11 are located on the same straight line along a lengthwise direction 1a of the left atrial appendage occluder 1, and the proximal end portion 111 and the distal end portion 112 of the seal disc 11 and the convergent end portion 121 are all located on this straight line.

The conical part 122 has a cone vertex and a distal-end opening end. The cone vertex is the above-mentioned convergent end portion 121. The distal-end opening end rolls up towards the proximal end from inside to outside and is connected with one end of the anchoring part 123. The other end of the anchoring part 123 is a suspended end. The anchoring part 123 is of an approximately cylindrical shape and surrounds the conical part 122. In a used state of the occluder 1, the conical part 123 is in contact with the cavity wall of the left atrial appendage. The suspended end of the anchoring part 123 is close to the distal end of the seal disc 11 and forms an opening. In one embodiment, the suspended end of the anchoring part 123 may be also inwards bent at a position close to the convergent end portion 121 to form an approximately U-shaped convergent region 124 surrounding the convergent end portion 121. Namely, in this example, the occluder 1 includes the conical part 122, the anchoring part 123 and the convergent region 124.

During the actual preparation of the anchoring apparatus 12, a steel jacket is arranged at one end of a woven mesh tube in a sleeving manner, and the steel jacket and the weaving wires are welded in a melted manner or style, so as to form the end portion 121. Then, the woven mesh tube is arranged on a mold in a sleeved manner, and the cone vertex of the mold is manipulated or moved to get close to the end portion 121 for heat setting, so as to form the conical part 122 and the anchoring part 123. In other embodiments, the anchoring part 123 also may be of other shapes besides the cylindrical shape as long as it achieves an effect of fixing the seal disc 11.

The first thin-film body 13 may partially or all cover the distal-end opening 1221 of the conical part 122. In the embodiment as shown in FIG. 1, the first thin-film body 13 is a spherical thin film which all covers the opening 1221 of the conical part 122. The first thin-film body 13 may further extend to cover the outer surface of at least one part of the distal end of the anchoring part 123. It can be understood that in other exemplary embodiments, the first thin-film body 13 may include at least one annular thin film which is fixed on the outer surface of at least one part of the distal end of the anchoring part 123, surrounds the opening 1221 of the conical part 122 and exposes at least one part of the opening of the conical part 122. In any exemplary embodiment of the above-mentioned position relations between the first thin-film body 13 and the anchoring part 123, the first thin-film body 13 at least covers one part of the outer surface of the distal end of the anchoring apparatus 12.

A thrombus may be prevented from passing through the first thin-film body 13, but a small amount of blood flow can be allowed to pass through the first thin-film body 13, or both the thrombus and the blood flow may be prevented from passing through the first thin-film body 13. The first thin-film body 13 may have multiple open pores. By means of setting an aperture ratio and/or an aperture size, the first thin-film body 13 has a permeation function, which allows blood flow to pass through and block thrombi. The surface of the first thin-film body 13 also may be plated or covered with an anticoagulant (heparin) or other compounds, or may be further treated so as to achieve the characteristic of antithrombin.

For the first thin-film body 13 having the open pores, the aperture range may be between about 65 and about 1000 microns. It can be understood that the aperture also may be slightly more than 1000 microns or slightly less than about 65 microns as long as it may prevent the thrombus from passing through. For example, the aperture may be specifically 65 to 400 microns. The aperture ratio of the first thin-film body 13 is a percentage of the area of the open pores to the whole area of the first thin-film body 13, and may be at least about 20 percent, specifically any one from about 25 to about 60 percent, which may be set as required. The first thin-film body 13 may be a two-dimensional sieve, a multi-pore film body, a woven or nonwoven mesh, or a similar structure. The first thin-film body 13 may be a metal having the above-mentioned permeation function or a metal mesh having thin fibers, or also may be made of a biocompatible material, such as ePFTE (such as Gortex®), polyester (such as Dacron®), PTFE (such as Teflon®), silicon resin, urethane, metal fibers or other biocompatible polymers, so that no more details will be described herein.

Figure 3:
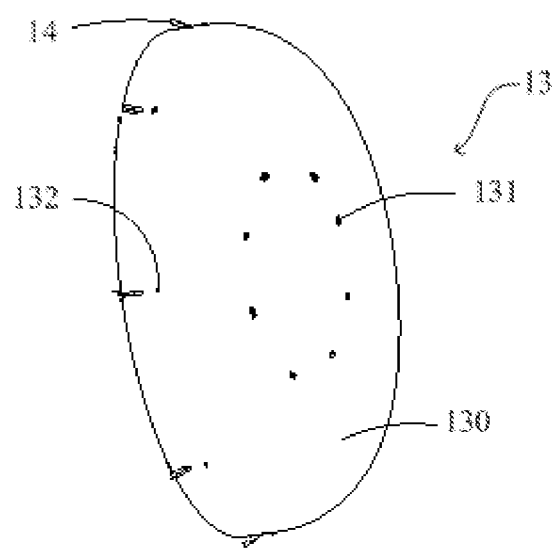
FIG. 3 is an exemplary structure schematic diagram showing the anchoring apparatus and a first thin-film body of FIG. 1.

The first thin-film body 13 may be sutured or adhered onto the outer surface of the distal end of the anchoring apparatus 12. In the specific embodiment as shown in FIGS. 1 to 3, the first thin-film body 13 is sutured and fixed on the anchoring apparatus 12. Referring to exemplary FIGS. 1 to 3 together, the first thin-film body 13 includes a semispherical thin film 130 which is sutured and fixed on the anchoring apparatus 12, all covers the opening 1221 of the conical part 122 and is partially located on the anchoring part 123. The thin film 130 may be fixed on the anchoring apparatus 12 through multiple suture points. For example, the thin film 130 is sutured onto the anchoring apparatus 12 through multiple first suture points 131 and multiple second suture points 132. The multiple first suture points 131 surround the conical part 122, and any one of the first suture points 131 is closer to the center axis of the anchoring apparatus 12 than any one of the second suture points 132. It can be understood that a connecting line of the multiple first suture points 131 is located outside the maximum diameter position of the opening of the conical part 122. In the embodiment, the multiple first suture points 131 and the multiple second suture points 132 may be all located on a circumference coaxial with the center axis of the anchoring apparatus 12. In other words, the connecting line of the multiple first suture points 131 and the connecting line of the multiple second suture points 132 are two concentric circles or substantially concentric circles.

For the anchoring apparatus 12 having the mesh structure, each of the above-mentioned suture points may be located at an intersection of two weaving wires 120. For example, a suture may be adopted to penetrate through the first thin-film body 13 (such as the thin film 130 in FIG. 3) and bypass the intersections of the weaving wires 120, and is knotted to fix the first thin-film body 13 onto the anchoring apparatus 12. In addition, when the first thin-film body 13 has the open pores, each hole may further facilitate suturing of the first thin-film body 13. For example, the suture also may penetrate through the open pores, thereby improving the firmness of suturing and preventing the suture from tearing the first thin-film body 13 as much as possible.

Referring still to exemplary FIGS. 1 through 3, at least one barb 14 is also arranged on the anchoring part 123. For example, each barb 14 may be arranged on at least one of the roll-up region of the conical part 122 and the anchoring part 123. Each barb 14 may be made of a material which is the same as that of the anchoring apparatus 12. For example, a nickel-titanium metal wire or a nickel-titanium metal rod may be fixed on the anchoring apparatus 12 through a sleeve 15. The root part of each barb 14 is connected with the anchoring apparatus 12. The end, opposite to the root part, of each barb 14 is a suspended end which faces to the seal disc 11 in the naturally expanded state.

The suspended end of each barb 14 also may penetrate through the first thin-film body 13. That is to say, the first thin-film body 13 also may be fixed on the anchoring apparatus 12 through each barb 14. For example, the length of each barb 14 beyond the first thin-film body 13 is in a range from about 1 mm to about 5 mm. In another exemplary embodiment, the length is in a range from about 1 mm to about 3 mm A distance from the edge of the proximal end of the first thin-film body 13 to the root part of each barb is in a range from about 1 mm to about 8 mm. In one embodiment, the distance is in a range from about 1 mm to about 5 mm. The thickness of a region, located near to each barb 14, of the thin-film body 13 can be greater than or equal to that of the rest region of the thin-film body 13.

After the above-mentioned occluder is implanted into the left atrial appendage, the anchoring apparatus is implanted into the cavity of the left atrial appendage, and the first thin-film body is in contact with the cavity wall of the left atrial appendage, thereby avoiding direct contact between the weaving wires and the cavity wall of the left atrial appendage and buffering a friction force from the weaving wires to the cavity wall of the left atrial appendage. Compared with a way that the weaving wires are in direct contact with the cavity wall of the left atrial appendage, this way enlarges the contact area of the first thin-film body by dozens of times, so that stress on the cavity wall of the left atrial appendage is more uniform, and each barb may uniformly puncture into the cavity wall of the left atrial appendage. In addition, the stress of a unit area is lower, which avoids injury to the cavity wall of the left atrial appendage caused by extremely high partial stress.

Further, for the anchoring apparatus of the mesh structure, to reduce injury to human blood vessels, the left atrial appendage occluder is required to be delivered to a selected part through a relatively thin delivery sheath. In addition, to reduce insertion and removal resistance (or "get-in" and "get-out" resistance) and ensure that the device may be put into the sheath successfully, it may correspondingly be desired or needed that the diameter of the anchoring apparatus in a compressed state, namely the sum of the wire diameters of the weaving wires forming the anchoring apparatus, is relatively small. These clinical requirements result in that a radial supporting force of the anchoring apparatus of the woven mesh structure is low relative to a framework structure formed by cutting one metal tube, namely the whole anchoring apparatus is relatively "soft", as understood by a person of ordinary skill in the art. The framework structure formed by cutting one nickel-titanium, namely the structure is formed by cutting the metal tube from its end portion along a direction towards the other end portion into multiple metal rods, bending each metal rod from the distal end to the proximal end and performing heat setting, such as a fixed frame structure disclosed in CN201110146287.5. If thicker weaving wires or weaving wires with relatively high rigidity are used to improve the radial supporting force of the mesh structure, a relatively thick delivery sheath is required, and the weaving wires with the high rigidity keep rubbing the cavity wall of the left atrial appendage, leading to exudation in the cavity wall of the left atrial appendage, which causes hydropericardium and even cardiac arrest. The relatively low radial supporting force corresponding to the anchoring apparatus of the mesh structure decides that the anchoring apparatus may have difficulty to maintain its original expanded appearance under the extrusion action of the cavity wall of the left atrial appendage after the device is implanted. That is to say, in a case of no first thin-film body, the anchoring apparatus formed by the mesh structure deforms easily after being implanted into the cavity of the left atrial appendage, which may cause the following disadvantages: the anchoring apparatus pulls the seal disc connected to it, which causes displacement or offset of the seal disc, resulting in that the seal disc may not be clung to the opening of the left atrial appendage, thereby forming a blood leaking channel between the cavity of the left atrial appendage and the left atrium, which directly results in a thrombus in the cavity of the left atrial appendage entering the left atrium. All the weaving wires in the anchoring apparatus can move and overall deform easily due to the lack of mutual constraint, so that the anchoring apparatus is hard or difficult to be located in the cavity of the left atrial appendage firmly. Furthermore, irregularity of the shape of the cavity of the left atrial appendage may lead to non-uniform stress on each point, thereby resulting in poor or loose fitment and potentially easily causing the device to fall out. In exemplary embodiments of the present application, the first thin-film body is arranged on the anchoring apparatus, which constrains a distance between the weaving wires to be constant all the time so as to constrain the deformation of different parts of the anchoring apparatus and accordingly improves the radial supporting force of the device to enable the anchoring apparatus to maintain a spread appearance in a natural state after the implantation so as to avoid the deformation of the anchoring apparatus as much as possible, thereby overcoming at least the above-mentioned two disadvantages.

Further, the root part of each barb extends out of the first thin-film body by a certain distance, so that when the barb punctures towards the cavity wall of the left atrial appendage and penetrates into the cavity wall by a certain depth, the whole first thin-film body may achieve a certain obstruction and control effect on the puncture of the barb so as to achieve a result of effectively controlling the puncture depth of the barb into the cavity wall of the left atrial appendage and reduce excessive injury to the cavity wall of the left atrial appendage caused by the non-uniform stress. In addition, under an extreme condition that a certain barb punctures through the cavity wall of the left atrial appendage, in case of no first thin-film body, blood in the left atrial appendage may permeate into the pericardial cavity from the punctured position, thereby causing the hydropericardium, and even causing the cardiac arrest and endangering the life in a severe case. However, for the present application, once the cavity wall of the left atrial appendage is punctured through by the barb, the first thin-film body may cover the punctured position immediately and contribute to a growth of tissues nearby at the same time, so as to quickly occlude the punctured hole, prevent the blood from permeating into the pericardial cavity and reduce the risk of the hydropericardium and even the cardiac arrest.

Further, compared with a left atrial appendage occluder without the first thin-film body on the anchoring apparatus, the left atrial appendage occluder in the present application has the advantage that when the seal disc may not completely cover the inlet of the left atrial appendage and the thrombus flows into the cavity of the left atrial appendage, the first thin-film body may form a second barrier in the cavity of the left atrial appendage to prevent the thrombus flowing into the cavity of the left atrial appendage from entering a deeper part in the cavity of the left atrial appendage, thereby decreasing the number of thrombi between the first thin-film body and the deeper part in the cavity of the left atrial appendage. Furthermore, the relatively thin deeper part of the left atrial appendage is extremely easy to injure under continuous impact of the thrombus, thereby causing the hydropericardium and even pericardial tamponade. Therefore, a space region surrounded by the first thin-film body and the seal disc may achieve a buffer effect, so as to achieve an effective protecting result on the deeper part in the cavity of the left atrial appendage and reduce the possibility of thrombosis. In addition, the first thin-film body in the present application at least prevents part of the thrombi from entering the space between the first thin-film body and the seal disc, so that the impact force of the thrombi in the cavity of the left atrial appendage to the seal disc is reduced, the service, useful, or effective life of the seal disc is prolonged, and then the service life of the left atrial appendage occluder is prolonged.

Further, if the first thin-film body has multiple open pores, it further facilitates outflow of the blood flowing into the cavity of the left atrial appendage and prevents the blood from staying in the deeper part in the cavity of the left atrial appendage, such as a "wing tip" position, thereby reducing the injury to the cavity of the left atrial appendage caused by blood pressure.

Referring back to exemplary FIG. 1, in one embodiment of the present application, the left atrial appendage occluder 1 further includes a second thin-film body 16 arranged in the seal disc 11. The second thin-film body 16 includes at least one thin film which is basically the same as the cross section of the seal disc 11 in size, and may be sutured and fixed into the seal disc 11. The second thin-film body 16 may be made of a material with high biocompatibility, such as PET (polyethylene terephthalate), PTFE (polytetrafluoroethylene), silica gel, or the like. The second thin-film body 16 may be an impervious film, which may basically prevent the blood flow and the thrombi in the blood flow at the same time. The second thin-film body 16 also may have multiple open pores. Through the setting of an aperture ratio and/or an aperture size, the second thin-film body 16 has a permeation function, which allows blood to pass through and blocks thrombi of relatively large sizes. The surface of the second thin-film body 16 also may be plated or covered with an anticoagulant (such as heparin) or other compounds, or may be further treated so as to achieve the characteristic of antithrombin.

For the second thin-film body 16 having the open pores, the aperture range may be about 65 to about 1000 microns. It can be understood that the aperture also may be slightly more than 1000 microns or slightly less than 65 microns as long as it may prevent the thrombus from passing through. For example, the aperture may be specifically 65 to 400 microns. The aperture ratio of the second thin-film body 16 is a percentage of the area of the open pores to the whole area of the second thin-film body 16, and is at least about 20 percent, for example, anywhere from 25 to 60 percent, which may be set as required or desired. The structure of the second thin-film body 16 may be a two-dimensional sieve, a multi-pore film body, a woven or nonwoven mesh, or a similar structure. The second thin-film body 16 may be a metal having the above-mentioned permeation function or a metal mesh having thin fibers. For example, the second thin-film body 16 also may be made of a biocompatible material, including ePFTE (such as Gortex®), polyester (such as Dacron®), PTFE (such as Teflon®), silicon resin, urethane, metal fibers or other biocompatible polymers, as desired, so that no more details will be described here.

The second thin-film body 16 and the first thin-film body 13 may be made of the same material or different materials. The first thin-film body 13 and the second thin-film body 16 may have the open pores at the same time. The apertures and the aperture ratios of the two thin film bodies may be adjusted to be the same or different as required, and various combinations will be no longer described one by one. For example, the aperture ratio of the first thin-film body 13 is slightly greater than that of the second thin-film body 16 and/or the aperture of the first thin-film body 13 is slightly greater than that of the second thin-film body 16. It should be noted that this implementation mode is only for an example, but not intended to limit the present application. A person of ordinary skill in the art can reasonably select the material of the first thin-film body 13 and the material of the second thin-film body 16 according to a requirement.

For example, the first thin-film body 13 and the second thin-film body 16 have multiple open holes at the same time. The multi-pore second thin-film body 16 may allow the blood flow to flow in the left atrial appendage and flow between the left atrial appendage and the atriums, thereby reducing pressure differences in the left atrial appendage and between the left atrial appendage and the atriums. The reduction of the pressure differences is favorable for recovery of a patient after the implanting operation of the left atrial appendage occluder 1. More specifically, when the blood flow flows between the left atrial appendage and the atriums, the heart of the patient gradually adapts to a human environment, where the left atrial appendage occluder 1 exists, more easily. When the second thin-film body 16 allows the blood to normally flow into the cavity of the left atrial appendage, the thrombus formed in the cavity of the left atrial appendage is blocked by the second thin-film body 16 and stays in the cavity, so as to prevent thrombus-induced apoplexy. At the same time, the first thin-film body 13 enlarges the contact area of the anchoring apparatus and the blood to achieve the buffer effect on the blood inflows, thereby avoiding, as much as possible, untight, loose, or ill-fitting closure of the seal disc caused by the deformation of the anchoring apparatus due to a fact that the blood inflows impact the occluder 1. In addition, compared with an anchoring apparatus without the first thin-film body 13, the anchoring apparatus 12 with the first thin-film body 13 lowers the flow rate of the blood flow in the cavity of the left atrial appendage. Therefore, under the condition that the contractile frequency of the atriums is constant, the volume of blood flowing into the deeper part of the left atrial appendage may be reduced, the possibility of thrombosis is further reduced, and the deeper part of the left atrial appendage is protected from being injured as much as possible.

All the technical features of the above-mentioned implementation modes may be combined as desired. To make the descriptions concise, all possible combinations of all the technical features in the above-mentioned implementation modes are not described. However, the combinations of these technical features shall all be deemed as with the scope of the present application as long as they have no contradictions.

The above implementation modes only express a few of implementation modes of the present application, and their descriptions are relatively specific and detailed, but shall not be regarded as limitations to the scope of the invention. It should be noted that people of ordinary skill in the art can further make a number of deformations, changes, variations, and improvements without departing from the idea of the present application, and these deformations, changes, variations, and improvements shall all fall within the protection scope of the present application.

The invention claimed is:

1. A left atrial appendage occluder, formed with a split structure, comprising:
   a proximal end configured to be an end close an operator in a surgical process and a distal end configured to be an end away from an operator in a surgical process;
   a seal disc and a mesh anchoring apparatus with a smaller radial supporting force which are connected with each other, wherein the anchoring apparatus extends from the seal disc towards the distal end to form a conical part having a distal-end opening, and the conical part rolls up towards the proximal end and then extends towards the proximal end to form an anchoring part, a suspended end of the anchoring part being located proximate to the seal disc; and the left atrial appendage occluder further comprises a thin-film body fixed on an outer surface of at least one part of the anchoring part, and at least part of the thin-film body covers the distal-end opening; the anchoring apparatus is formed by multiple weaving wires; the thin-film body can restrict deformation of different parts of the anchoring apparatus, and enhance the radial supporting force of the anchoring apparatus.

2. The left atrial appendage occluder according to claim 1, wherein the thin-film body comprises a spherical thin film which completely covers the distal-end opening and is fixed on the outer surface of at least one part of the anchor part at the distal end.

3. The left atrial appendage occluder according to claim 1, wherein the thin-film body comprises at least one annular thin film surrounding the distal-end opening, and each annular thin film is fixed on the outer surface of at least one part of the anchoring part and exposes the distal-end opening.

4. The left atrial appendage occluder according to claim 1, wherein the thin-film body is one of sutured or adhered onto the anchoring apparatus.

5. The left atrial appendage occluder according to claim 1, wherein the thin-film body is made of polyester, PTFE (polytetrafluoroethylene), silicon resin, urethane, metal fibers or silica gel.

6. The left atrial appendage occluder according to claim 1, wherein the thin-film body has multiple open pores.

7. The left atrial appendage occluder according to claim 6, wherein each pore has an aperture of 65 to 1000 microns.

8. The left atrial appendage occluder according to claim 6, wherein the aperture ratio of the thin-film body is at least 20 percent.

9. The left atrial appendage occluder according to claim 1, wherein the anchoring part surrounds the conical part, and the suspended end of the anchoring part is inwards bent to form an approximately U-shaped convergent region.

10. The left atrial appendage occluder according to claim 1, wherein the anchoring part is provided with at least one barb, a suspended end of the at least one barb faces to the seal disc.

11. The left atrial appendage occluder according to claim 10, wherein the suspended end of the at least one barb penetrates through the thin-film body.

12. The left atrial appendage occluder according to claim 11, wherein a distance from an edge of an end of the thin-film body facing the proximal end to a root part of each barb is 1 mm to 8 mm.

13. The left atrial appendage occluder according to claim 11, wherein after penetrating through the thin-film body, each barb extends out of the thin-film body by a length of 1 mm to 5 mm.

14. The left atrial appendage occluder according to claim 11, wherein the thickness of a region, located near to each barb, of the thin-film body is greater than or equal to that of other regions of the thin-film body.

15. The left atrial appendage occluder according to claim 1, wherein at an intersection of two weaving wires of the anchoring apparatus, the thin-film body is sutured onto the anchoring apparatus.

16. The left atrial appendage occluder according to claim 15, wherein a suture penetrates through the thin-film body, bypasses an intersection of weaving wires and is knotted to fix the thin-film body onto the anchoring apparatus.

17. The left atrial appendage occluder according to claim 15, wherein the thin-film body is fixed on the anchoring part on the anchoring apparatus through multiple first suture points and multiple second suture points, the multiple first suture points surround the distal-end opening, and at least one of the first suture points is closer to the distal-end opening than any one of the second suture points.

18. The left atrial appendage occluder according to claim 17, wherein the multiple first suture points and the multiple second suture points are respectively located on two circumferences coaxial with the anchoring apparatus.

19. The left atrial appendage occluder according to claim 1, wherein the center axis of the seal disc and the center axis of the anchoring apparatus are located on the same straight line along a lengthwise direction.

20. The left atrial appendage occluder according to claim 1, wherein another thin-film body is further arranged in the seal disc and has multiple open pores, each pore having an aperture of 65 microns to 1000 microns.

* * * * *